US009089875B2

(12) United States Patent
Jin et al.

(10) Patent No.: US 9,089,875 B2
(45) Date of Patent: Jul. 28, 2015

(54) ULTRASOUND BACKING ELEMENT, TRANSDUCER AND ULTRASOUND PROBE INCLUDING THE SAME

(71) Applicant: Samsung Medison Co., Ltd., Gangwon-do (KR)

(72) Inventors: Gil-Ju Jin, Gangwon-do (KR); Mi-Ri Kim, Gangwon-do (KR); Min-Seon Seo, Gangwon-do (KR); Hae-Ran Choi, Gangwon-do (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 318 days.

(21) Appl. No.: 13/687,940

(22) Filed: Nov. 28, 2012

(65) Prior Publication Data

US 2014/0145561 A1    May 29, 2014

(30) Foreign Application Priority Data

Mar. 7, 2012   (KR) .......................... 10-2012-023620

(51) Int. Cl.
   *H01L 41/053* (2006.01)
   *B06B 1/06* (2006.01)
   *A61B 8/00* (2006.01)

(52) U.S. Cl.
   CPC ............. *B06B 1/0674* (2013.01); *A61B 8/4405* (2013.01); *A61B 8/4444* (2013.01); *A61B 8/4483* (2013.01)

(58) Field of Classification Search
   CPC .... H04R 17/00; B06B 1/0603; B06B 1/0622; H03H 9/09; F16F 15/005; G10K 11/002; G10K 11/30
   USPC .................................. 310/326, 327, 334, 335
   See application file for complete search history.

(56) References Cited

U.S. PATENT DOCUMENTS

| 6,418,084 | B2 * | 7/2002 | Saito et al. .................... 367/152 |
| 7,694,406 | B2 * | 4/2010 | Wildes et al. ................... 29/594 |
| 2006/0181177 | A1 * | 8/2006 | Osawa .......................... 310/322 |
| 2006/0191342 | A1 * | 8/2006 | Renzel ............................ 73/597 |
| 2008/0303381 | A1 * | 12/2008 | Yuuya et al. ................... 310/327 |
| 2009/0069691 | A1 * | 3/2009 | Saito ............................. 600/459 |
| 2010/0013358 | A1 * | 1/2010 | Nakayama .................... 310/348 |

FOREIGN PATENT DOCUMENTS

| JP | 2004214734 A | 7/2004 |
| JP | 2006101901 A | 4/2006 |
| JP | 2006254406 A | 9/2006 |
| JP | 2009-038675 A | 2/2009 |

OTHER PUBLICATIONS

Korean Notice of Allowance issued in Application No. 10-2012-0023620 dated Jan. 17, 2014.

* cited by examiner

*Primary Examiner* — Derek Rosenau
*Assistant Examiner* — Bryan Gordon
(74) *Attorney, Agent, or Firm* — McDermott Will & Emery LLP

(57) ABSTRACT

An ultrasound backing element, a transducer including the ultrasound backing element, and an ultrasound probe. The ultrasound backing element includes: a first concave/convex unit formed of a material capable of absorbing ultrasonic waves, and comprising a first surface and a second surface that are not in parallel with each other; and a first electrode unit comprising a first electrode and a second electrode that are respectively disposed on the first surface and the second surface.

18 Claims, 9 Drawing Sheets

ULTRASOUND BACKING ELEMENT, TRANSDUCER AND ULTRASOUND PROBE INCLUDING THE SAME

CROSS-REFERENCE TO RELATED PATENT APPLICATION

This application claims the benefit of Korean Patent Application No. 10-2012-0023620, filed on Mar. 7, 2012, in the Korean Intellectual Property Office, the disclosure of which is incorporated herein in its entirety by reference.

BACKGROUND OF THE INVENTION

1. Field of the Invention

The present invention relates to an ultrasound backing element, a transducer including the ultrasound backing element, and an ultrasound probe.

2. Description of the Related Art

In general, ultrasonic diagnosis apparatuses irradiate ultrasonic waves to a subject such as a living body of a human being or an animal, detect an echo signal reflected in the living body to display a tomogram of an organ in the living body, and provide information that is necessary to diagnose the subject.

Here, the ultrasonic diagnosis apparatus includes an ultrasound probe for transmitting the ultrasonic wave into the subject and for receiving the echo signal from the subject.

In addition, the ultrasound probe includes a transducer that is mounted therein for converting an ultrasonic signal into an electric signal and vice versa. In general, the transducer includes a collection of a plurality of ultrasonic oscillators.

Therefore, the ultrasonic diagnosis apparatus having the above structure irradiates the ultrasonic wave to the subject and converts a reflected ultrasonic signal to an electric signal. Then, the ultrasonic diagnosis apparatus transmits the converted electric signal to an image processing apparatus and generates an image by using a signal transmitted from the image processing apparatus.

The ultrasonic diagnosis apparatus using the ultrasound probe is used in medical fields for detecting foreign substances in a living body, measuring a degree of injury, observing tumors, and observing fetuses, through the above described processes.

The conventional ultrasound probe includes a backing unit that is close to a piezoelectric element so that the backing unit absorbs noise wavelengths generated from the piezoelectric element to prevent the noise from transferring to the piezoelectric element. However, it is difficult to eliminate the noise wavelength completely. Therefore, technologies for addressing the above problem are necessary.

SUMMARY OF THE INVENTION

The present invention provides an ultrasound backing element including electrodes therein, a transducer including the ultrasound backing element, and an ultrasound probe.

The present invention also provides an ultrasound backing element in which electrodes are arranged not to be parallel with each other, a transducer including the ultrasound backing element, and an ultrasound probe.

According to an aspect of the present invention, there is provided an ultrasound backing element including: a first concave/convex unit formed of a material capable of absorbing ultrasonic waves, and including a first surface and a second surface that are not in parallel with each other; and a first electrode unit including a first electrode and a second electrode that are respectively disposed on the first surface and the second surface.

The ultrasound backing element may further include a second concave/convex unit formed of a material capable of absorbing ultrasonic waves and engaged with the first concave/convex unit to be complementary with the first concave/convex unit while the first electrode unit is interposed between the first and second concave/convex units.

The ultrasound backing element may further include a third concave/convex unit formed of a material capable of absorbing ultrasonic waves and engaged with the first concave/convex unit to be complementary with the first concave/convex unit in a same shape as the first concave/convex unit while the first electrode unit is interposed between the first and third concave/convex units.

The ultrasound backing element may further include a filling unit formed of a material capable of absorbing ultrasonic waves and filling a space between the first and third concave/convex units.

The first electrode unit may have a multi-layered structure.

The first and second electrodes may be separated from each other.

The first concave/convex unit may further include a separator that separates the first and second surfaces from each other.

The separator may be formed as a groove that is concave toward inside of the first concave/convex unit.

The separator may be formed as a plane that is not in parallel with the first and second surfaces.

The first and second surfaces may be connected to each other, and the first and second electrodes may be disposed on some parts of the first and second surfaces to be separated from each other.

The ultrasound backing element may further include upper electrodes disposed on a front surface of the first concave/convex unit and connected to the first electrode unit.

The upper electrodes may be separated from each other.

The first surface and the second surface may be symmetrical to each other.

The first and second surfaces may be arranged repeatedly.

According to another aspect of the present invention, there is provided a transducer including: a piezoelectric element unit including a plurality of piezoelectric elements for converting ultrasonic signals into electric signals and vice versa while vibrating; and an ultrasound backing element for supporting the piezoelectric element unit and absorbing some of ultrasonic waves generated by the piezoelectric element unit.

The plurality of piezoelectric elements may be arranged in a one-dimensional manner.

The plurality of piezoelectric elements may be arranged in a two-dimensional manner.

According to another aspect of the present invention, there is provide an ultrasound probe including: a housing; and a transducer disposed in the housing.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
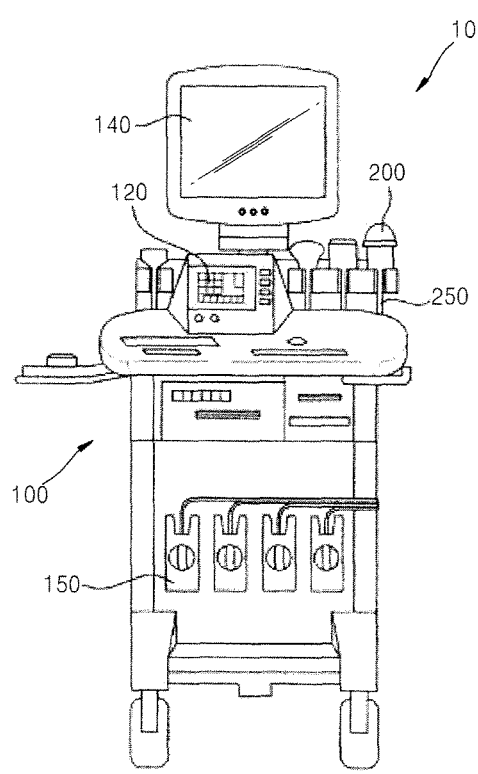
FIG. 1 is a front view of an ultrasonic diagnosis apparatus including an ultrasound probe according to an embodiment of the present invention.

Hereinafter, the present invention will be described in detail by explaining preferred embodiments of the invention with reference to the attached drawings. Like reference numerals in the drawings denote like elements. Expressions such as "at least one of," when preceding a list of elements, modify the entire list of elements and do not modify the individual elements of the list.

FIG. 1 is a front view of an ultrasonic diagnosis apparatus 10 including an ultrasound probe 200 according to an embodiment of the present invention. The ultrasound probe 200 of the present embodiment may be used in various ultrasound probe-related apparatuses, as well as in the ultrasonic diagnosis apparatus 10. Hereinafter, a case where the ultrasound probe 200 of the present embodiment is used in the ultrasonic diagnosis apparatus will be described as an example for convenience of description.

Referring to FIG. 1, the ultrasonic diagnosis apparatus 10 according to the present embodiment includes a main body 100 in which a manipulation button 120 and a display apparatus 140 are provided to generate an image of a subject, and the ultrasound probe 200 irradiating ultrasonic waves to the subject and receiving ultrasonic echo from the object. The ultrasound probe 200 is connected to the main body 100 by a cable 250 that is integrally connected to the ultrasound probe 200 and a connector 150.

Figure 2:
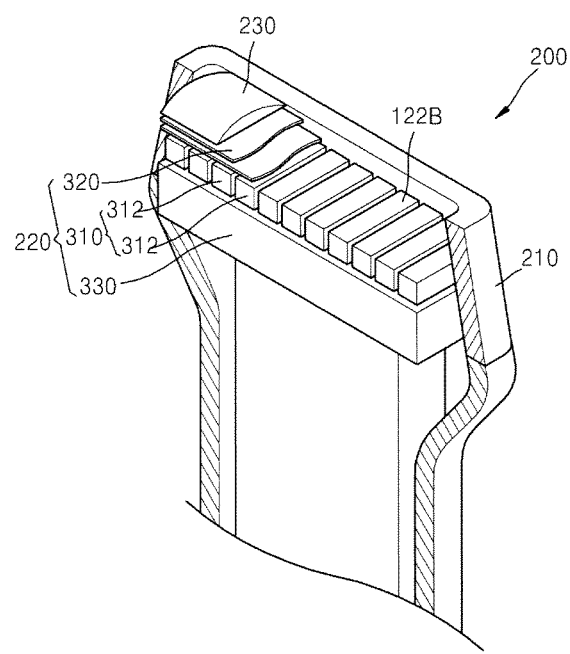
FIG. 2 is a partially cut perspective view schematically showing an inner structure of the ultrasound probe of FIG. 1.

FIG. 2 is a partially cut perspective view schematically showing in inner structure of the ultrasound probe 200 according to the embodiment of the present invention.

As shown in FIG. 2, the ultrasound probe 200 of the present embodiment includes a housing 210 forming a body and a transducer 220 disposed in the housing 210 for generating ultrasonic waves according to a voltage applied from the ultrasonic diagnosis apparatus 100. In addition, the ultrasound probe 200 may further include an acoustic lens 230 for condensing the ultrasonic waves.

The transducer 220 includes a piezoelectric element unit 310 converting an electric signal and an acoustic signal to each other, a matching unit 320 matching an acoustic impedance of the ultrasonic wave generated by the piezoelectric element unit 310 to an acoustic impedance of the object, and an acoustic backing unit 330 absorbing the ultrasonic waves transmitted to an opposite side of the object.

The piezoelectric element unit 310 includes at least one piezoelectric device 312 for converting the electric signal and the acoustic signal to each other while vibrating. The piezoelectric devices 312 may be formed by dividing a piezoelectric material into a plurality of pieces. For example, the piezoelectric devices 312 may be fabricated by performing a dicing process of the piezoelectric material that is elongated in a lengthwise direction. However, the method of fabricating the plurality of piezoelectric devices 312 is not limited to the above example, that is, the piezoelectric devices 312 may be formed by pushing the piezoelectric material with a metal mold. The piezoelectric material may be a piezoelectric ceramic, a piezoelectric single-crystal, and a composite piezoelectric material combining the above materials and a polymer.

The matching unit 320 is disposed on a front surface of the piezoelectric element unit 310, and gradually changes the acoustic impedance of the ultrasonic wave generated by the piezoelectric element unit 310 to be similar to that of the subject. Here, the front surface of the piezoelectric element unit 310 may be a surface of the piezoelectric element unit 310, which is the closest to the subject, while the ultrasonic wave is transmitted to the subject, and a rear surface is an opposite surface of the front surface.

The matching unit 320 may be elongated along with the front surface of the piezeoelectric element unit 310; however, the present invention is not limited thereto, that is, the matching unit 320 may be formed partially on the front surface of the piezoelectric element unit 310. In addition, the matching unit 320 has a single layered structure in the present embodiment; however, the matching unit 320 may be formed to have a multi-layered structure.

The acoustic backing unit 330 supports the piezoelectric devices 312 from rear surfaces of the piezoelectric devices 312, and may absorb the ultrasonic waves that are transmitted to a rear portion of the piezoelectric element unit 310 and not used directly in the examination or diagnosis. The acoustic backing unit 330 may have the same length as that of the piezoelectric element unit 310 in the lengthwise direction of the piezoelectric element unit 310. Here, the lengthwise direction may denote a direction along longer sides of the piezoelectric element unit 310 as shown in FIG. 2. A plurality of electrodes for applying a voltage to the piezoelectric element unit 310 may be formed in the acoustic backing unit 330. Since the electrodes are respectively connected to the piezoelectric devices 312, the number of the electrodes may be the same as the number of piezoelectric devices 312. The acoustic backing unit 330 may be also referred to as an ultrasonic wave backing element (hereinafter, referred to as 'ultrasound backing element'). The ultrasound backing element 330 will be described in more detail later.

The acoustic lens 230 is disposed on a front surface of the transducer 220, and condenses the ultrasonic wave generated by the piezoelectric element unit 310. The acoustic lens 230 may be formed of a material such as silicon rubber having an acoustic impedance that is close to that of the subject. In addition, a center portion of the acoustic lens 230 may be convex or flat. The acoustic lens 230 may be formed in various shapes according to a design of a designer.

Figure 3A:
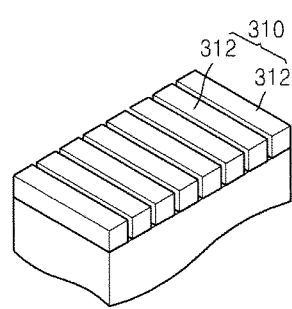
FIGS. 3A and 3B are diagrams showing arrangements of piezoelectric elements in a piezoelectric element unit according to an embodiment of the present invention.
Figure 3B:
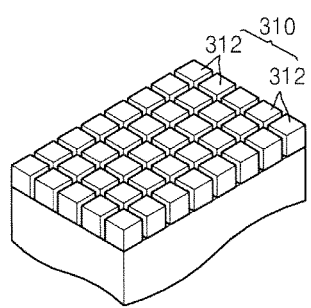

FIGS. 3A and 3B are diagrams showing arrangements of the piezoelectric devices 312 in the piezoelectric element unit 310 according to the present embodiment.

As shown in FIG. 3A, the piezoelectric devices 312 may be arranged on the front surface of the acoustic backing device 330 in a one-dimensional manner along a lengthwise direction of the piezoelectric element unit 310. This may be referred to as a one-dimensional piezoelectric device unit. The one-dimensional piezoelectric device unit may be a linear array or a curved array. The arrangement type may be set variously depending on an intension of the designer. The one-dimensional piezoelectric device unit is easily manufactured, and thus manufacturing costs may be reduced. However, it is difficult to realize a three-dimensional image by using the one-dimensional piezoelectric device unit.

As shown in FIG. 3B, the piezoelectric devices 312 may be arranged in a two-dimensional manner, that is, in the lengthwise direction of the piezoelectric element unit 310 and in a direction perpendicular to the lengthwise direction. This may be referred to as a two-dimensional piezoelectric device unit. The two-dimensional piezoelectric device unit may be a linear array or a curved array. The arrangement type may be set variously depending on intension of the designer. Here, the two-dimensional piezoelectric device unit appropriately delays input times of signals that are respectively input in the piezoelectric devices 312 and transmit the signals to the subject along an external scanning line for transmitting the ultrasonic wave. Therefore, a three-dimensional image may be obtained by using a plurality of echo signals.

In addition, as the number of the piezoelectric devices 312 increases, a clearer ultrasonic wave image may be obtained. In order to increase the number of the piezoelectric devices 312, there is a need to reduce sizes of the piezoelectric devices 312, and accordingly the electrodes have to be effectively arranged on the piezoelectric devices 312 via the ultrasound backing element 330 of a narrow area. In order to arrange the electrodes effectively, the electrodes may be arranged in the ultrasound backing element 330 to be inclined with respect to the others.

Figure 4:
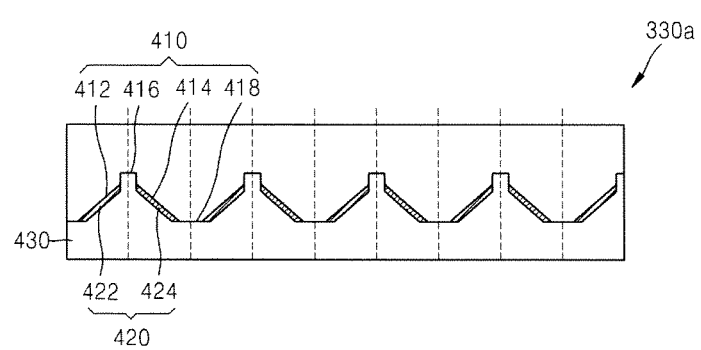
FIG. 4 is a plan view of an ultrasound backing element according to an embodiment of the present invention.
Figure 5:
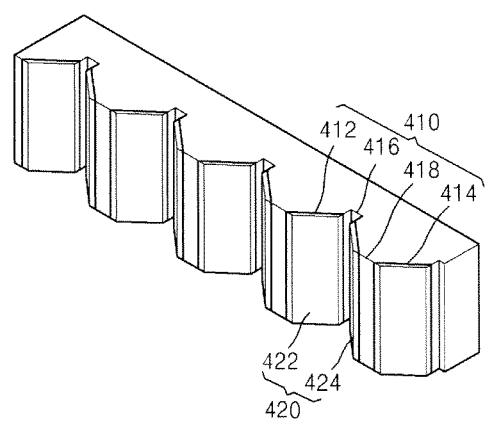
FIG. 5 is a perspective view of a first concave/convex unit, on a side surface of which electrodes are arranged, in the ultrasound backing element of FIG. 4.

FIG. 4 is a plan view of an ultrasound backing element 330a according to an embodiment of the present invention, and FIG. 5 is a perspective view of a first concave/convex unit 410, on a side surface of which electrodes are arranged, in the ultrasound backing element 330a shown in FIG. 4.

As shown in FIGS. 4 and 5, the ultrasound backing element 330a may include the first concave/convex unit 410 including at least two surfaces that are not in parallel with each other and a first electrode unit 420 including at least two electrodes respectively disposed on the two surfaces of the first concave/convex unit 410. In addition, the ultrasound backing element 330a may include a second concave/convex unit 430 that is engaged with the first concave/convex unit 410 to be complementary with the first concave/convex unit 410 while the electrodes are interposed between the first and second concave/convex units 410 and 430.

The first concave/convex unit 410 may include a first surface 412 and a second surface 414 that are not parallel with each other. The first and second surfaces 412 and 414 may be symmetrical to each other. However, the present embodiment is not limited thereto, that is, the first and second surfaces 412 and 414 may not be symmetrical to each other. A first separator 416 and a second separator 418 may be further formed between the first and second surfaces 412 and 414 for separating the first and second surfaces 412 and 414 from each other. The first separator 416 may be formed as a groove that is concave toward inside of the first concave/convex unit 410, and the second separator 418 may be formed as a flat surface that is not parallel with the first and second surfaces 412 and 414. However, the present invention is not limited thereto, that is, the first separator 416 may be formed as a flat surface and the second separator 418 may be formed as a groove. Otherwise, the first and second separators 416 and 418 may not be formed. In addition, the first and second surfaces 412 and 414 that are not parallel with each other may be repeatedly arranged. The first concave/convex unit 410 may be formed of an attenuating material having a low acoustic impedance.

The first electrode unit 420 may include a first electrode 422 disposed on the first surface 412 and a second electrode 424 disposed on the second electrode 414. Since the first and second surfaces 412 and 414 are not parallel with each other, the first and second electrodes 422 and 424 disposed respectively on the first and second surfaces 412 and 414 are not parallel with each other. In addition, the first and second electrodes 422 and 424 may be separated from each other. When the first concave/convex unit 410 includes the first and second separators 416 and 418, each of the first and second electrodes 422 and 424 may be formed on at least a part of each of the first and second surfaces 412 and 414. However, when the first concave/convex unit 410 does not include at least one of the first and second separators 416 and 418, each of the first and second electrodes 422 and 424 may be respectively formed on a part of each of the first and second surfaces 412 and 414. Thus, the first and second electrodes 422 and 424 may be separated from each other. The first and second electrodes 422 and 424 may be formed of a conductive material. The first and second electrodes 422 and 424 may be elongated similarly to a band or a rod.

In FIGS. 4 and 5, the first and second surfaces 412 and 414 that are not parallel with each other are repeatedly formed, and the electrodes 422 and 424 are respectively formed on the first and second surfaces 412 and 414. However, the present invention is not limited thereto, that is, three or more surfaces that are not parallel with each other are formed, and electrodes may be respectively formed on the three or more surfaces.

The first concave/convex unit 410 and the first electrode unit 420 may be fabricated as follows. A substrate formed of an attenuating material is etched to form a concave/convex pattern. The concave/convex pattern may be a pattern in which a 'V' shape is repeatedly arranged, or may be formed having other shapes. In addition, a conductive material is deposited on the concave/convex pattern. Next, boundaries of the concave/convex pattern are cut so that the conductive material may be partitioned. For example, edges of concave portions in the concave/convex pattern are cut as grooves that are concave toward inside the substrate, and edges of convex portions in the concave/convex pattern are cut so as to be planar. Then, the conductive material is partitioned into a plurality of electrodes. Another way of forming the electrodes is to attach a mask, in which holes that have the same shape as the first electrode 420 are formed, onto the substrate on which the concave/convex pattern is formed, and to coat a conductive material on portions that are exposed via the holes of the mask to form the first electrode unit 420.

The second concave/convex unit 430 may have a complementary shape with respect to the first concave/convex unit 410, while the first electrode unit 420 is interposed between the first and second concave/convex units 410 and 430. In addition, the second concave/convex unit 430 is engaged with the first concave/convex unit 410. The second concave/convex unit 430 may be formed of an attenuating material having a low acoustic impedance that may absorb the ultrasonic wave. The first concave/convex unit 410 on which the first electrode unit 420 is formed is disposed in a mold having the same shape as an outer appearance of the ultrasound backing element 330a, and the attenuating material is filled in the mold to contact the first concave/convex unit 410 while interposing the first electrode unit 420 between the attenuating material and the first concave/convex unit 410. In addition, the attenuating material is hardened to form the second concave/convex unit 430.

As described above, since the electrodes are arranged so as not to be in parallel with each other, a lot of electrodes may be formed in the same area when compared with the parallel electrodes.

Figure 6:
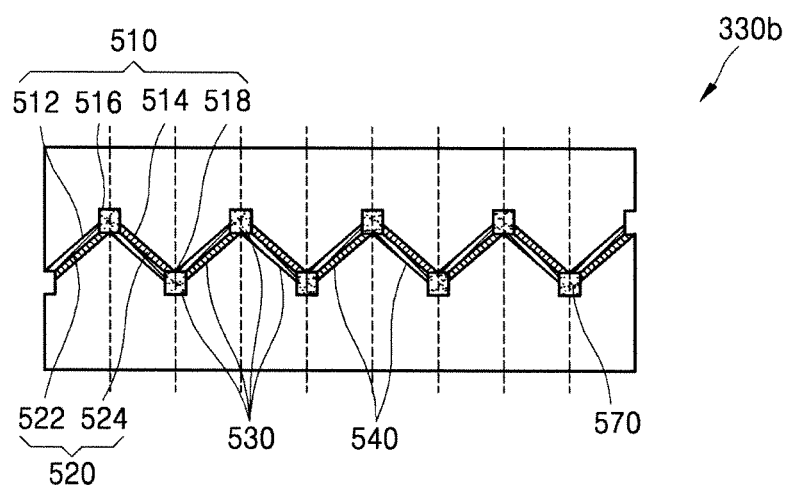
FIG. 6 is a plan view of an ultrasound backing element according to another embodiment of the present invention.

FIG. 6 is a plan view of an ultrasound backing element 330b according to another embodiment of the present invention. Referring to FIG. 6, the ultrasound backing element 330b may include a third concave/convex unit 510 including at least two surfaces that are not parallel with each other, and a second electrode unit 520 including electrodes that are respectively disposed on the at least two surfaces. In addition, the ultrasound backing element 330b may further include a fourth concave/convex unit 530 that has the same shape as the third concave/convex unit 510 and is engaged with the third concave/convex unit 510 complementary with each other, and a third electrode unit 540 disposed between the second electrode unit 520 and the fourth concave/convex unit 530 and coupled to the second electrode unit 520.

The third concave/convex unit 510 may have the same structure as the first concave/convex unit 410 shown in FIG. 4. For example, the third concave/convex unit 510 may include a third surface 512 and a fourth surface 514 that are not parallel with each other. A third separator 516 and a fourth separator 518 may be further formed between the third and fourth surfaces 512 and 514 for separating the third and fourth surfaces 512 and 514 from each other. The third separator 516 may be formed as a groove that is concave toward inside of the third concave/convex unit 510, and the fourth separator 518 may be formed to be planar and not parallel with the third and fourth surfaces 512 and 514. However, the present invention is not limited thereto, that is, the third separator 516 may be formed to be planar and the fourth separator 518 may be formed as a groove.

Otherwise, the third and fourth separators 516 and 518 may not be formed. The third concave/convex unit 510 may be formed of an attenuating material having a low acoustic impedance.

The second electrode unit 520 may include a third electrode 522 disposed on the third surface 512 and a fourth electrode 524 disposed on the fourth electrode 514. Since the third and fourth surfaces 512 and 514 are not parallel with each other, the third and fourth electrodes 522 and 524 disposed respectively on the third and fourth surfaces 512 and 514 are not parallel with each other. In addition, the third and fourth electrodes 522 and 524 may be separated from each other. When the third concave/convex unit 510 includes the third and fourth separators 516 and 518, each of the third and fourth electrodes 522 and 524 may be formed on an entire portion of each of the third and fourth surfaces 512 and 514. However, when the third concave/convex unit 510 does not include at least one of the third and fourth separators 516 and 518, each of the third and fourth electrodes 522 and 524 may be respectively formed on a part of each of the third and fourth surfaces 512 and 514. Thus, the third and fourth electrodes 522 and 524 may be separated from each other. The third and fourth electrodes 522 and 524 may be formed of a conductive material. The third and fourth electrodes 522 and 524 may be elongated similarly to a band or a rod.

The fourth concave/convex unit 530 and the third electrode unit 540 have the same structures as those of the third concave/convex unit 510 and the second electrode unit 520, respectively. The fourth concave/convex unit 530 is complementarily engaged with the third concave/convex unit 510, and the second electrode unit 520 and the third electrode unit 540 contact each other. Since the second and third electrode units 520 and 530 contact each other to function as one electrode having a multi-layered structure, a cross-sectional area of the electrode contacting the piezoelectric device 312 may be increased. The third concave/convex unit 510 on which the second electrode unit 520 is formed and the fourth concave/convex unit 530 on which the third electrode unit 540 is formed may be fabricated in the same way as that of the first concave/convex unit 410 on which the first electrode unit 420 is formed.

Moreover, the ultrasound backing element 330b may further include a filling unit 570 filling a space between the third concave/convex unit 510 and the fourth concave/convex unit 530. The filling unit 570 may be formed of the attenuating material having a low acoustic impedance. The filling unit 570 may be formed by coupling the third concave/convex unit 510 on which the second electrode unit 520 is disposed and the fourth concave/convex unit 530 on which the third electrode unit 540 is disposed to be complementary with each other, and depositing the attenuating material in the space between the third and fourth concave/convex units 510 and 530.

Figure 7A:
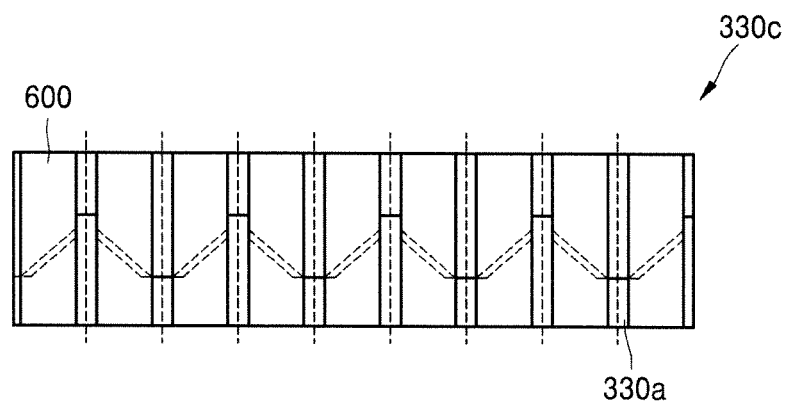
FIGS. 7A and 7B are diagrams of an ultrasound backing element including an upper electrode.
Figure 7B:
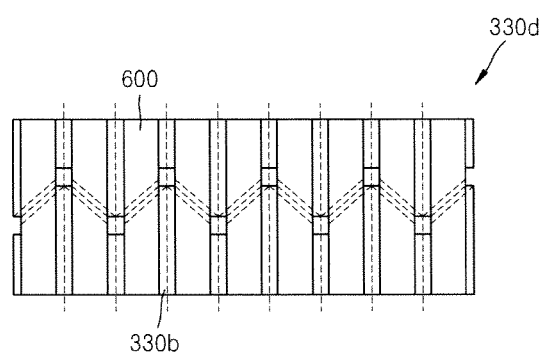

An upper electrode may be further disposed on a front surface of the ultrasound backing element 330a or 330b for allowing the electrodes in the ultrasound backing element 330 to sufficiently apply voltages to the piezoelectric devices 312. FIGS. 7A and 7B are diagrams showing ultrasound backing elements 330c and 330d including upper electrodes 600.

FIG. 7A shows a state where the upper electrodes 600 are additionally disposed on an upper surface of the ultrasound backing element 330a shown in FIG. 4. The upper electrodes 600 may correspond to the electrodes of the first electrode unit 420 in a one-to-one correspondence. In addition, the upper electrodes 600 may be separated from each other. A cross-sectional area of the upper electrode 600 may be equal to or less than that of the piezoelectric device 312.

FIG. 7B shows a state where the upper electrodes 600 are additionally disposed on an upper surface of the ultrasound backing element 330b shown in FIG. 6. The upper electrodes 600 may correspond to the electrodes of the first electrode unit 420 or the second and third electrode units 520 and 540 in a one-to-one correspondence. In addition, the upper electrodes 600 may be separated from each other. A cross-sectional area of the upper electrode 600 may be equal to or less than that of the piezoelectric device 312.

The upper electrodes 600 may be fabricated as follows. After fabricating the ultrasound backing element 330a or 330b shown in FIG. 4 or FIG. 6, a conductive material is deposited on the front surface of the ultrasound backing element 330a or 330b. In addition, a piezoelectric material is deposited on a front entire surface of the conductive material. Then, the piezoelectric material and the conductive material are diced so that one piezoelectric device 312 may correspond to one of the electrodes in the ultrasound backing element 330a or 330b, and then the piezoelectric element unit 310 and the upper electrodes 600 are fabricated.

On the other hand, the ultrasound backing elements 300a, 300b, 300c, or 300d supports the one-dimensional piezoelectric element unit 310. However, the ultrasound backing element 330a, 330b, 330c, or 330d may support the two-dimensional piezoelectric device unit.

Figure 8A:
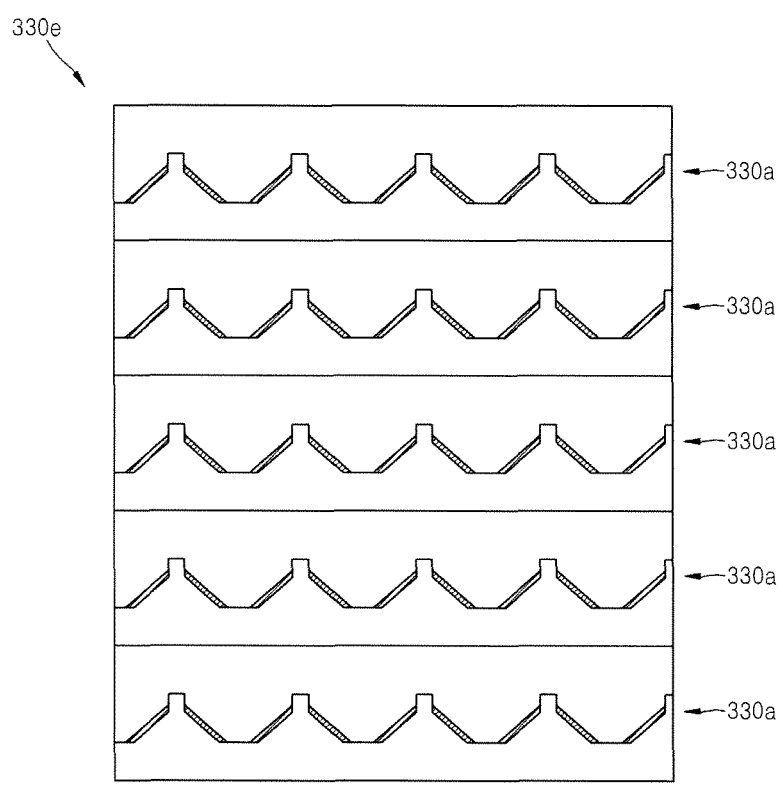
FIGS. 8A and 8B are diagrams showing an ultrasound backing element supporting a two-dimensional piezoelectric element unit.
Figure 8B:
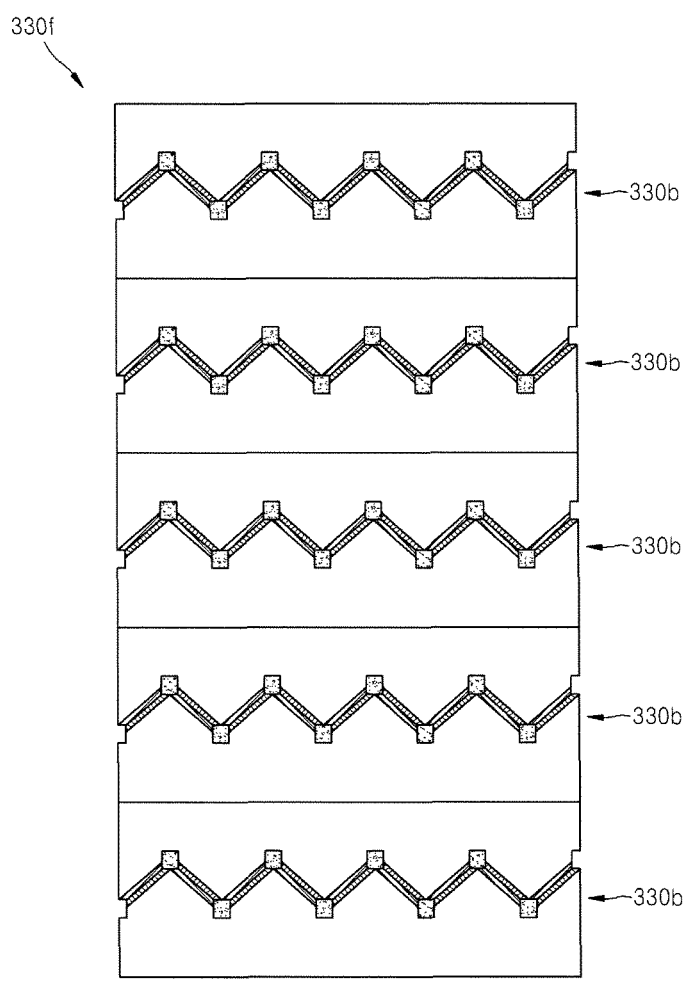

FIGS. 8A and 8B are diagrams showing ultrasound backing elements 330e and 330g supporting the two-dimensional piezoelectric device unit.

As shown in FIG. 8A, a plurality of the ultrasound backing elements 330a shown in FIG. 4 may be arranged in a direction that is perpendicular to a lengthwise direction of the ultrasound backing element 330a. The ultrasound backing element 330e of FIG. 8A may support the two-dimensional piezoelectric device unit. Otherwise, as shown in FIG. 8B, a plurality of ultrasound backing elements 330b shown in FIG. 6 may be arranged in a direction that is perpendicular to the lengthwise direction of the ultrasound backing element 330b. The ultrasound backing element 330g shown in FIG. 8B may support the two-dimensional piezoelectric device unit. Otherwise, although not shown in the drawings, a combination of the ultrasound backing element 330a shown in FIG. 4 and the ultrasound backing element 330b shown in FIG. 6 may support the two-dimensional piezoelectric device unit. In addition, upper electrodes may be further disposed between the two-dimensional piezoelectric device unit and the ultrasound backing element.

So far, the concave/convex portion of the ultrasound backing element includes the first surface and the second surface that are not in parallel with each other, and the electrodes are formed on the first and second surfaces. The first and second surfaces that are not in parallel with each other may be symmetrical to each other based on the first or second separator. However, the present invention is not limited thereto. That is, the first and second surfaces that are not in parallel with each other may be asymmetrical to each other based on at least one of the first and second separators.

Figure 9:
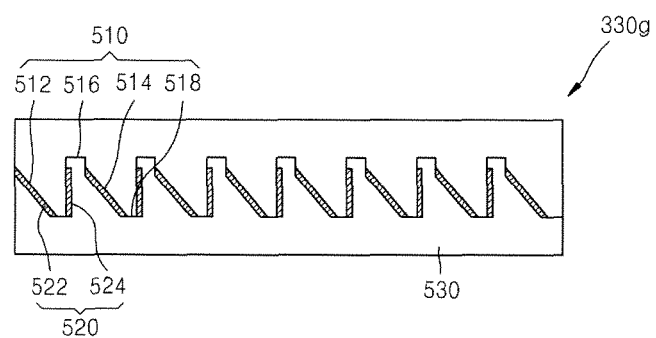
FIG. 9 is a plan view of an ultrasound backing element having a first surface and a second surface that are asymmetrical to each other and not parallel with each other according to an embodiment of the present invention.

FIG. 9 is a plan view of an ultrasound backing element 330g having a first surface and a second surface that are not in parallel with each other and asymmetrical to each other according to another embodiment of the present invention.

As shown in FIG. 9, the ultrasound backing element 330g includes a first concave/convex unit 510 including at least two surfaces that are not in parallel with each other, and a first electrode unit 520 including electrodes that are respectively disposed on the at least two surfaces. In addition, the ultrasound backing element 330g may include a second concave/convex unit 530 that is engaged with the first concave/convex unit 510 to be complementary with each other, while the electrodes are interposed between the first and second concave/convex units 510 and 530.

The first concave/convex unit 510 may include a first surface 512 and a second surface 514 that are not in parallel with each other. The first and second surfaces 512 and 514 are asymmetrical to each other. For example, the first surface 512 may be perpendicular to a lengthwise direction of the ultrasound backing element 330g, and the second surface 514 may be inclined with respect to the lengthwise direction of the ultrasound backing element 330g. A first separator 516 and a second separator 518 may be further formed between the first and second surfaces 512 and 514 for separating the first and second surfaces 512 and 514 from each other. The first separator 516 may be formed as a groove that is concave toward inside of the first concave/convex unit 510, and the second separator 518 may be formed to be planar and not in parallel with the first and second surfaces 512 and 514.

The first electrode unit 520 may include a first electrode 522 disposed on the first surface 512 and a second electrode 524 disposed on the second surface 514. Since the first and second surfaces 512 and 514 are not in parallel with each other, the first and second electrodes 522 and 524 that are respectively disposed on the first and second surfaces 512 and 514 are not in parallel with each other. In addition, the first and second electrodes 522 and 524 may be separated from each other. When the first concave/convex unit 510 includes the first and second separators 516 and 518, each of the first and second electrodes 522 and 524 may be formed on at least a part of each of the first and second surfaces 512 and 514. The first and second electrodes 522 and 524 may be formed of a conductive material. The first and second electrodes 522 and 524 may be formed to be elongated similarly to a band or rod shape.

The second concave/convex unit 530 may have a complementary shape with respect to the first concave/convex unit 510, while the first electrode unit 520 is interposed between the first and second concave/convex units 510 and 530. In addition, the second concave/convex unit 530 may be engaged with the first concave/convex unit 510. The second concave/convex unit 530 may be formed of an attenuating material having a low acoustic impedance for absorbing ultrasonic waves.

As described above, since electrodes are disposed in the ultrasound backing element, acoustic loss and distortion may be reduced. In addition, since the electrodes are arranged not to be in parallel with each other, a lot of electrodes may be formed, and accordingly a small sized ultrasound backing element, transducer, and probe may be manufactured and an accurate ultrasound image may be obtained.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasound backing element comprising:
   a first concave/convex unit formed of a material capable of absorbing ultrasonic waves, and comprising a first surface and a second surface that are not in parallel with each other; and
   a first electrode unit comprising a first electrode and a second electrode that are respectively disposed on the first surface and the second surface.

2. The ultrasound backing element of claim 1, further comprising a second concave/convex unit formed of a material capable of absorbing ultrasonic waves and engaged with the first concave/convex unit to be complementary with the first concave/convex unit while the first electrode unit is interposed between the first and second concave/convex units.

3. The ultrasound backing element of claim 1, further comprising a third concave/convex unit formed of a material capable of absorbing ultrasonic waves and engaged with the first concave/convex unit to be complementary with the first concave/convex unit in a same shape as the first concave/convex unit while the first electrode unit is interposed between the first and third concave/convex units.

4. The ultrasound backing element of claim 3, further comprising a filling unit formed of a material capable of absorbing ultrasonic waves and filling a space between the first and third concave/convex units.

5. The ultrasound backing element of claim 1, wherein the first electrode unit has a multi-layered structure.

6. The ultrasound backing element of claim 1, wherein the first and second electrodes are separated from each other.

7. The ultrasound backing element of claim 1, wherein the first concave/convex unit further comprises a separator that separates the first and second surfaces from each other.

8. The ultrasound backing element of claim 7, wherein the separator is formed as a groove that is concave toward inside of the first concave/convex unit.

9. The ultrasound backing element of claim 7, wherein the separator is formed as a plane that is not in parallel with the first and second surfaces.

10. The ultrasound backing element of claim 1, wherein the first and second surfaces are connected to each other, and the first and second electrodes are disposed on some parts of the first and second surfaces to be separated from each other.

11. The ultrasound backing element of claim 1, further comprising upper electrodes disposed on a front surface of the first concave/convex unit and connected to the first electrode unit.

12. The ultrasound backing element of claim 11, wherein the upper electrodes are separated from each other.

13. The ultrasound backing element of claim 1, wherein the first surface and the second surface are symmetrical to each other.

14. The ultrasound backing element of claim 1, wherein the first and second surfaces are arranged repeatedly.

15. A transducer comprising:
a piezoelectric element unit comprising a plurality of piezoelectric elements for converting ultrasonic signals into electric signals and vice versa while vibrating; and
an ultrasound backing element according to claim 1 for supporting the piezoelectric element unit and absorbing some of ultrasonic waves generated by the piezoelectric element unit.

16. The transducer of claim 15, wherein the plurality of piezoelectric elements are arranged in a one-dimensional manner.

17. The transducer of claim 15, wherein the plurality of piezoelectric elements are arranged in a two-dimensional manner.

18. An ultrasound probe comprising:
a housing; and
a transducer according to claim 15 disposed in the housing.

* * * * *